United States Patent [19]

Cohen et al.

[11] Patent Number: 4,802,491

[45] Date of Patent: Feb. 7, 1989

[54] METHOD AND APPARATUS FOR ASSESSING MYOCARDIAL ELECTRICAL STABILITY

[75] Inventors: Richard J. Cohen, Newton Highlands; Joseph M. Smith, Brookline, both of Mass.

[73] Assignee: Massachusetts Institute of Technology, Cambridge, Mass.

[21] Appl. No.: 891,653

[22] Filed: Jul. 30, 1986

[51] Int. Cl.$^4$ .............................................. A61B 5/04
[52] U.S. Cl. ................................ 128/702; 364/413.06
[58] Field of Search ............................. 364/415, 417; 128/702–704, 680

[56] References Cited

U.S. PATENT DOCUMENTS

| | | | |
|---|---|---|---|
| 3,759,248 | 9/1973 | Valiquette | 128/703 |
| 3,902,479 | 9/1975 | Chaumet | 128/703 |
| 4,170,992 | 10/1979 | Dillman | 128/702 |
| 4,603,703 | 8/1986 | McGill et al. | 364/417 |
| 4,665,485 | 5/1987 | Lundy et al. | 128/702 |

OTHER PUBLICATIONS

Sim et al., "Australasian Physical Sciences in Medicine", vol. 2–6, No. 83, Aug. 1979, pp. 340–345.

Dower et al., "Computers in Cardiology Conference", Rotterdam, Netherlands, Sep. 29–Oct. 1, 1977, pp. 497–501.

"Period Multupling—Evidence for Nonlinear Behaviour of the Canine Heart" by A. L. Ritzenberg et al., Nature, vol. 307, No. 5947, pp. 159–161, 1/12/84.

"Computers in Cardiology" by J. M. Smith et al., Abstract, presented Sep. 8–11, 1985, Linkoping, Sweden.

"Estimation of Ventricular Vulnerability to Fibrillation Through T-Wave Time Series Analysis" by D. R. Adam et al., reprinted Com. in Card., pp. 307–310, 9/1981.

"Fluctuations in T-Wave Morphology and Susceptibility to Ventricular Fibrillation" by D. R. Adam et al., J. Electrocard., 17 (3), 1984, pp. 209–218.

"Ventricular Fibrillation and Fluctuations in the Magnitude of the Repolarization Vector" by D. R. Adam et al., Reprinted IEEE 1982, Comp. in Card. 1982, pp. 241–244.

Primary Examiner—William E. Kamm

[57] ABSTRACT

Myocardial electrical stability is assessed based on the derivation of an alternating ECG morphology index from a series of heartbeats. The ECG electrical signal waveform is digitized at a pluralty of sample points for each of the series of beats. Sample point matrices from the digitized ECG signals are constructed and the alternating energy at each of the sample points for the series of beats is computed. The alternating energy over the entire set of sample points is summed to generate the total alternating energy. This total alternating energy is normalized with respect to the energy of the average waveform, the normalized value being the alternating ECG morphology index. Animal studies indicate a high negative correlation between cardiac electrical stability and the alternating ECG morphology index.

17 Claims, 2 Drawing Sheets

DATA ANALYSIS SCHEME

FIG. 1: DATA ANALYSIS SCHEME

METHOD AND APPARATUS FOR ASSESSING MYOCARDIAL ELECTRICAL STABILITY

The Government has rights in this invention pursuant to Contract Number N00014-80-C-0520 awarded by the Department of the Navy.

BACKGROUND OF THE INVENTION

This invention relates to method and apparatus for assessing the electrical stability of the heart, and more particularly to the generation of an alternating ECG morphology index having strong correlation with myocardial electrical stability.

Sudden cardiac death, defined as death resulting from cardiac cause within 24 hours of onset of symptoms, has been referred to as the most challenging problem facing contemporary cardiology. Most sudden deaths are unexpected, unheralded by symptoms of any duration or by overt coronary artery disease. In the United States alone, sudden cardiac death typically claims between 400,000 and 500,000 lives each year, and represents the major cause of death for men between the ages of 20 and 64.

It is thought that the mechanism responsible for the great majority of sudden cardiac deaths is ventricular fibrillation, a state in which the normally organized electrical activity of the heart becomes disorganized and apparently chaotic. This disorganized electrical activity initiates similarly disorganized and ineffectual mechanical contraction of the pumping chambers of the heart resulting in circulatory collapse and death.

By far the most desirable and potentially the most effective response to the problem of sudden cardiac death is prevention, in which the first step would necessarily be the identification of those individuals at increased risk. It is this identification with which the present invention is concerned.

One non-invasive technique for assessing the "cardiac status" of a given individual involves analysis of the alternation from beat-to-beat in the morphology of the electrocardiogram (ECG) complex. While it has been long hypothesized that a link exists between alternation in ECG morphology and myocardial electrical stability, the prior art techniques have been only marginally successful. The prior art comprehends the relationship of fluctuations in the T-wave morphology of the ECG complex with susceptibility to ventricular fibrillation. See, for example, "Fluctuations in T-Wave Morphology and Susceptibility to Ventricular Fibrillation," by Adam et al. in the *Journal of Electrocardiology* 17 (3), 1984, 209–218; "Estimation of Ventricular Vulnerability to Fibrillation Through T-Wave Time Series Analysis," by Adam et al., *Computers in Cardiology*, September 1981; "Ventricular Fibrillation and Fluctuations in the Magnitude of the Repolarization Vector," by Adam et al., IEEE, 1982 Computers in Cardiology. In these references, the alternation of T-wave energy from beat-to-beat was measured to generate a T-wave alternation index (TWAI). This technique, however, is unable to detect alternation in waveform morphology which results in alternating wave shapes of equal energy. Additionally, the amount of alternation detected was dependent on the specific static portion wave shape. Thus, the same amount of alternation superimposed on a different amplitude signal resulted in different values for the T-wave alternation index. This technique might even completely obscure the presence of alternation in the original waveform morphologies.

It is therefore an object of the present invention to provide method and apparatus for characterizing alternating ECG morphology useful for accessing myocardial electrical stability.

SUMMARY OF THE INVENTION

The present invention derives an alternating ECG morphology index from a series of heart beats. The ECG electrical signal waveform is digitized at a plurality of sample points for each of the beats. Sample point matrices are constructed from the digitized ECG signals. The alternating energy at each of the sample points for the series of beats is computed and the alternating energy over the entire set of sample points is summed to generate the total alternating energy. This total alternating energy is normalized with respect to the energy of the average waveform, the normalized value being the alternating ECG morphology index. Animal studies have shown a high correlation of decreased ventricular fibrillation threshold with increases in the alternating ECG morphology index.

BRIEF DESCRIPTION OF THE DRAWING

The invention disclosed herein will be understood better with reference to the drawing of which.

DESCRIPTION OF THE PREFERRED EMBODIMENT

Figure 1:
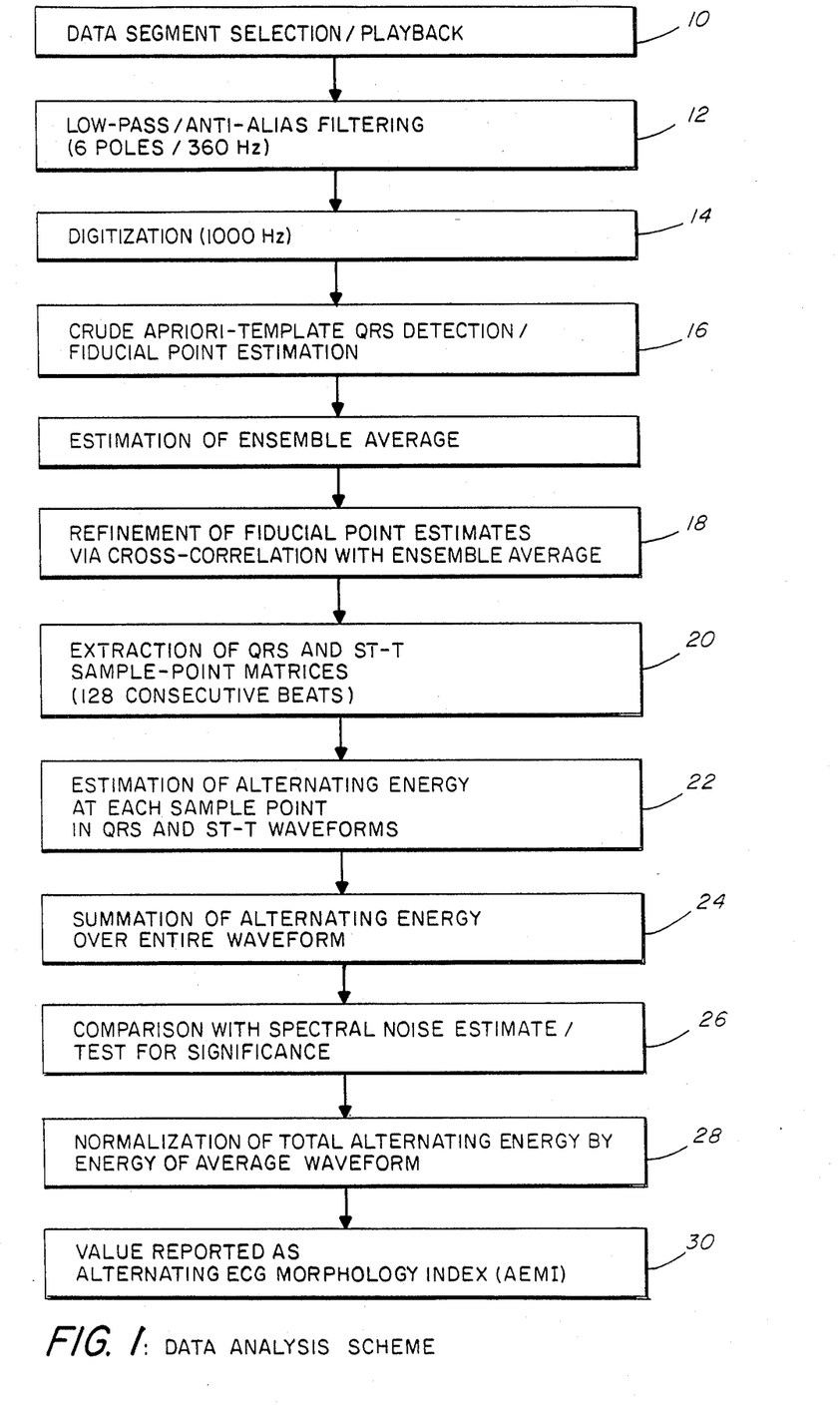
FIG. 1 is a block diagram of the data analysis scheme disclosed herein.

The overall data analysis scheme according to the present invention is depicted in FIG. 1. Analog electrical heartbeat signals are recorded, for example, on a Hewlett-Packard 3968a FM tape recorder. The appropriate data segments to be analyzed are selected in the data segment selection/playback block 10. The ECG output channels from the FM tape recorder are connected through 6-pole Butterworth low-pass filtering amplifiers 12 (cutoff frequency set to 360 Hz) to a Masscomp MC500 computer outfitted with a 16 channel multiplexer-analog-to-digital converter 14, a 166 Mbyte disk, and 2 Mbyte core memory. The ECG channels are sampled at a rate of 1000 samples per second and placed on disk in contiguous files. QRS or other ECG complexes are identified and fiducial points (timing markers corresponding to the location of each QRS complex) determined by a template matching scheme shown in block 16. See Moody, GB: ARISTOTLE: Ambulatory Real-Time Interactive System For Testing On Two Lead ECG's, MIT Bioengineering Center, May 30, 1983. Following this initial phase of QRS complex detection, a second refinement phase is initiated, wherein an iterative, adaptive template matching (matched filter) scheme 18 is employed to refine initial fiducial point estimates. A suitable waveform for this fine alignment scheme is the vector magnitude (square root of the sum of the squares of the three orthogonal leads) of the QRS complex, namely $$\text{Vector Magnitude of the } i^{th} \text{ QRS Complex} = m_{QRS}(i, nT) = [x_{QRS}^2(i, nT) + y_{QRS}^2(i, nT) + z_{QRS}^2(i, nT)]^{\frac{1}{2}}$$

where i is the index for the beat number, n is the index for sample number within a beat, and T is the time between adjacent samples.

Average QRS Vector Magnitude =

$$\overline{m}_{QRS}(nT) = \frac{1}{N} \sum_{i=0}^{N-1} m_{QRS}(i, nT)$$

With this average as a template, the fiducial points corresponding to each QRS complex are then shifted to maximize the cross-correlation between $\overline{m}_{QRS}(nT)$ and $m_{QRS}(i, nT)$. $\overline{m}_{QRS}(nT)$ is then recalculated based on the shifted fiducial points, and the process repeated until all fiducial point locations are stable. In practice, one pass through the alignment scheme is generally sufficient. At this point, the inter-epoch intervals are examined graphically for user-assisted detection and correction of missed epochs. Next, waveform segments (defined as the array of sampled value in a time window relative to the refined fiducial point) of sequential vector magnitude waveforms are examined for alternating morphology.

The analysis procedure used to detect and quantify alternation in waveform morphology consists of examining each sample point within the waveform segment of interest for alternation, and then integrating over the entire waveform segment. An example will illustrate salient features of this technique. Up to this point, there has been described an epoch detection/alignment procedure which will allow for the construction of a two dimensional matrix of sample values shown in block 20. The columns are indexed in terms of nT samples into the waveform segment (corresponding to time) and the rows are indexed in terms of i, beat number. Looking across in one row one would see the sampled values corresponding to, for example, a single QRS complex, $m_{QRS}(i_{fixed}, nT)$. Looking down a single column (down the ensemble at the same temporal offset from the fiducial marker), one would see the different values that the waveform took at one particular time in its evolution, $m_{QRS}(i, n_{fixed}T)$. If, for example, QRS peak amplitude were alternating on a beat-to-beat basis, one can identify this by locating the column corresponding to the time at which the QRS reached its peak, $n_{peak}T$, and then looking down that particular column (at the series corresponding to $m_{QRS}(i, n_{peak}T)$), for the alternation. If one were to model the waveform under study, m(i, nT), as consisting of a static part, s(i, nT), which is independent of i, and an alternating part, a(i, nT), which can be viewed as a fixed waveform with alternates polarity on a beat-to-beat basis $a(i, nT) = (-1)^i a(nT)$, then one can construct a method to quantify the amount of energy associated with a(i, nT), or simply $$\sum_n a^2(nT).$$

(Of course, actual waveforms also contain fluctuations which do not alternate on a beat-by-beat basis but vary from beat-to-beat in a more complex way. The method presented here permits the selective identification of the alternating component a(i, nT).) This is a marked improvement over prior art techniques. In the prior art techniques, the alternation present in waveform energy was studied, i.e., alternation in the series $$E_i = \sum_n m^2(i, nT)$$

or, expanding m(i, nT), $$E_i = \sum_n [s^2(i, nT) + 2s(i, nT)a(i, nT) + a^2(i, nT)]$$

The only alternating component in this constructed series is the cross term, 2s(i, nT)a(i, nT), since s(i, nT) is static with respect to i and $a^2(i, nT)$ is static because a(i, nT) only alternates in sign with i. Thus, the measured alternation in this series is very dependent on the form of s(i, nT), not just on a (i, nT). The effect of s(i, nT) could be to enhance, diminish, or even completely obscure the presence of alternation in the original waveform morphologies.

According to the present invention, a methodology will be described for measuring the energy of the alternating component present in a waveform. The difference, which may initially seem subtle, is extremely important. In earlier studies, alternation of waveform energies was measured which failed to detect alternation in waveform morphology resulting in alternating waveshapes of equal energy. Additionally, the amount of alternation detected was dependent on the specific static wave-shape. The same amount of alternation superimposed on a different amplitude signal resulted in a different value for the T-wave alternation index. If one measures the energy of the alternating component of the waveform, both these issues are addressed. Energy is a positive-definite metric, and as such, if alternation is present in the series of waveforms, its energy will always be a positive term. There is no opportunity for alternation present in the series of waveforms to be masked or enhanced by the particular form of the alternating component. Secondly, a measurement of the energy of the alternating component is independent of the specific wave-shape of the static component. One may wish later to scale the results by the energy of the static component to construct a proportional metric, but the initial metric of energy of the alternating component is independent of the underlying static wave-shape.

The method according to the present invention for measuring the energy of the alternating component of the series of waveforms will now be discussed. To this point, there has been described a technique for constructing a matrix of data, the columns corresponding to $m(i, n_{fixed}T)$ and the rows corresponding to $m(i_{fixed}, nT)$. If one estimates the alternating energy in the sequence $m(i, n_{fixed}T)$ via spectral techniques (i.e., calculate the discrete energy spectrum of the series), and repeats this for each sample point, n, and sums the alternating energy at each sample point over all sample points within the waveform, one will have succeeded in measuring the energy of the alternating component of m(i, nT). Namely, $$m(i, nT) = s(i, nT) + a(i, nT)$$

Sample Autocorrelation Function =

$$R_{m(i, n = n_0T), m(i + l, n = n_0T)} =$$

$$\frac{1}{N - l - 1} \sum_{i=0}^{N-l} m(i, n_0T) \cdot m(i + l, n_0T)$$

expanding m(i, $n_0T$) and m(i+l, $n_0T$), $$R_{m(i, n_0T), m(i+l, n_0T)} = \frac{1}{N-l-1} \sum_{i=0}^{N-l} [s(i, n_0T) + a(i, n_0T)] \cdot [s(i+l, n_0T) + a(i+l, n_0T)]$$

but, $s(i, n_0T)=s(i+l, n_0T)$, and $a(i, n_0T)=(-1)^l \cdot a(i+1, n_0T)$, and therefore $$R_{m(i, n_0T), m(i+l, n_0T)} = \frac{1}{N-l-1} \sum_{i=0}^{N-l} [s(i, n_0T) + a(i, n_0T)] \cdot [s(i+l, n_0T) + (-1)^l \cdot a(i, n_0T)]$$

Now, for l odd one has $$R_{m(i, n_0T), m(i+1, n_0T)} = \frac{1}{N-l-1} \sum_{i=0}^{N-l} s^2(i, n_0T) - a^2(i, n_0T)$$

and for l even one has $$R_{m(i, n_0T), m(i+1, n_0T)} = \frac{1}{N-l-1} \sum_{i=0}^{N-l} s^2(i, n_0T) + 2s(i, n_0T) \cdot a(i, n_0T) + a^2(i, n_0T)$$

but the cross term $2s(i, n_0T) \cdot a(i, n_0T)$ alternates its sign with i because $a(i, n_0T)$ alternates its sign with i; and because one is summing up an even number of these cross terms, their sum is zero. Thus, for l even one has $$R_{m(i, n_0T), m(i+1, n_0T)} = \frac{1}{N-l-1} \sum_{i=0}^{N-l} s^2(i, n_0T) + a^2(i, n_0T)$$

Regrouping terms, one has (for all l)

$$R_{m(i, n_0T), m(i+l, n_0T)} = \frac{1}{N-l-1} \sum_{i=0}^{N-l} s^2(i, n_0T) + (-1)^l \cdot a^2(i, n_0T)$$

If one now constructs the discrete Fourier transform of this autocorrelation function, estimating the discrete power spectrum, one arrives at Power Spectrum Estimate = $|Y_{n0}(k)|$ =

$$\left| \sum_{l=0}^{N-1} R_{m(i, n_0T), m(i+l, n_0T)} \cdot e^{-jlk\omega_0} \right|$$

where $\omega_0 = \frac{2\pi}{N}$ substituting for $R_{m(i, n_0T), m(i+1, n_0T)}$, and evaluating $|Y_{n0}(k)|$ at $k=N/2$, one has $$|Y_{n0}(k=N/2)| = \left| \sum_{l=0}^{N-1} [s^2(i, n_0T) + (-1)^l \cdot a^2(i, n_0T)] \cdot e^{-jl\pi} \right|$$

Recognizing that $e^{-jl\pi}=(-1)^l$, one has $|Y_{n0}(k=N/2)| =$ $$\left| \sum_{l=0}^{N-1} s^2(i, n_0T) \cdot (-1)^l + a^2(i, n_0T) \cdot (-1)^{2l} \right| = N \cdot a^2(i, n_0T)$$

Thus, by constructing the estimate of the discrete power spectrum of the series m(i, $n_0T$) with i indexed through the series of sequential beats from 0 to N, and evaluating this power spectrum at N/2 (corresponding to the frequency of alternation), one arrives at N times the energy of the alternating component at the value of $n_0$, block 22. It is clear that by carrying out this process for each value of n along the time-course of the waveform of interest, summing the results and dividing by N, the number of beats, one will arrive at the total energy of the alternating component, block 24, namely, $$\frac{1}{N} \sum_n |Y_n(k=N/2)| = \frac{1}{N} \sum_n N \cdot a^2(nT) =$$

$$\sum_n a^2(nT) = \text{energy of the alternating component}$$

This analysis has been carried out assuming that the only beat-to-beat variation in the ECG complex morphology is that of alternation $a(i, nT)=(-1)^i a(nT)$. However, the spectral method described is effective in separating the alternation component from other beat-to-beat variability in ECG complex morphology which are represented as contributions to the spectrum $Y_n(k)$ for values of $k<N/2$. The alternation component is revealed at the value $k=N/2$ corresponding to the Nyquist frequency. Thus, by computing the power spectrum estimate and evaluating its value at $k=N/2$, one can reliably identify the alternation component of the beat-to-beat variability in ECG complex morphology.

With the foregoing explanation complete, additional specific details of the method will now be addressed. For each aligned ECG epoch (QRS complex, ST segment and T wave) (N=128), the vector magnitude function is created. Two data matrices are then constructed, one corresponding to depolarization (QRS complex), here defined as a 100 millisecond window centered about the middle of the average QRS vector magnitude waveform, and one corresponding to repolarization (ST segment and T wave), here defined as the 200 millisecond window immediately following the end of the QRS window. The QRS data matrix thus consists of 128 rows (each corresponding to a successive QRS complex) and 100 columns (each column corresponding to one sample point during the QRS). The ST-T wave data matrix similarly has 128 rows, each corresponding to a different, but sequential ST-T wave, and 100 columns, here representing every other sample of the original ST-T waves. For each column in each of the data matrices, the power spectral estimate is calculated by constructing the discrete Fourier transform of the Hanning-windowed sample autocorrelation function. These estimates are then algebraically summed over all of the columns, thus generating one power spectrum for each of the two data matrices. The point in the aggregate power spectrum corresponding to alternation (Nyquist frequency) is compared, block 26, to an estimate of the noise in an adjacent spectral band by constructing the sample mean and sample standard deviation of 8 adjacent frequency samples in that band. A noise estimate is made in the frequency band located at 15/16ths of the alternating frequency. Alternation in morphology is judged significant if the power at the frequency of alternation exceeds the estimate of the noise mean by 3 standard deviations. It should be noted that because the variance of the power spectrum estimate is twice its normal value at both DC and at the frequency of alternation, the measure for significance is actually whether the power at the frequency of alternation exceeds the noise mean by $3 \times \sqrt{2}$ or 4.24 standard deviations. The value reported for the amount of alternation present is the noise corrected estimate of the energy of the alternating component divided by the energy of the average waveform. So, for the QRS complex, the noise corrected estimtate of the energy associated with the alternating waveform component is scaled, block 28, by the energy in the average vector QRS complex and is the Alternating ECG Morphology Index (AEMI) for the QRS, denoted as AEMI(QRS). For the ST-T wave, this has been denoted as AEMI(ST-T). The alternating ECG morphology index (AEMI) is reported at block 30.

Animal stuides conducted at the Massachusetts Institute of Technology have established a correlation between a decrease in ventricular fibrillation threshold (VFT) and an increase in the alternating electrocardiographic morphology index (AEMI). The details of these animal experiments will now be described.

Twenty (20) mongrel dogs, 15–25 kilograms in weight, were anesthetized with 1 mg/kg of acepromazine subcutaneously and 30 mg/kg of sodium pentobarbital (Nembutal) intraveneously. Additional Nembutal was given as needed to maintain deep anesthesia. Respiration was maintained by means of an air-cuffed endotracheal tube connected to a mechanical ventilator. Three pairs of transcutaneous needle electrodes were applied along the three cardinal (orthogonal) directions (lateral limb lead—X; rostral-caudal lead—Y; dorsal-ventral lead—Z) for the recording of the three orthogonal lead electrocardiogram (Electronics for Medicine ECG amplifier, bandpass 0.04–500 Hz). Systemic arterial pressure was monitored via an intra-arterial catheter connected to a Statham P23a transducer. The three ECG signals and the arterial pressure signal were recorded on a Hewlett-Packard 3968A 8-track FM instrumentation tape recorder with tape speed set to 3¾ ips (3 dB bandwidth of 0–1250 Hz).

The surgical preparation for each of the experiments was begun with a left lateral thoracotomy. The pericardium was incised and the heart was suspended in a pericardial cradle. One pair of barb-type pacing electrodes was applied to the left atrial appendage (for atrial pacing), and a pair of screw-type electrodes was applied to the left ventricular free wall between the first and second diagonal branches of the Left Anterior Descending (LAD) coronary artery (for VFT determination). The inter-electrode distance was set to be approximately 2 cm.

For the coronary occlusion studies, a 1 cm segment of the LAD just distal to the first diagonal branch was dissected free from the surrounding fascia, and an inflatable saline filled vascular occlusion cuff (In Vivo Metric, Healdsburg, CA, 954-48) was securely fastened around the artery. The pericardium was then loosely approximated, the muscle and skin layers were closed separately, and the chest was evacuated of air via a suction drainage tube. Following a recovery period of 30–45 minutes, ECG and blood pressure recordings were made at a variety of atrial pacing rates, with VFT determinations being made at the extremes of the ranges of pacing rates. Successive VFT determinations were separated by at least 15 minutes. Transient (10 minute) coronary artery occlusions were then conducted at each of the same pacing rages. VFT measurements were made between the third and fifth minute of occlusion. In the event of spontaneous ventricular fibrillation, the VFT was taken to be zero.

In the hypothermia experiments, a thermocouple was sutured in place within the pericardium, and the pericardium and chest were closed as described above. In addition, a counter-current heat exchanger was connected between the right femoral artery and the left femoral vein. Following a recovery period of 30–45 minutes, ECG and blood pressure recordings were made at several atrial pacing rates with VFT determinations again being made at the extremes of the range of pacing rates. The dogs were then anti-coagulated (heparin-100 ug/kg iv), and the femoral artery-femoral vein bypass heat exchanger was opened. The temperature of the counter-current flow was regulated so that the target temperature of 20° C. was reached in 90–120 minutes. At this temperature, the experimental protocol established under normothermic conditions was repeated as tolerated. Once data collection of hypothermic temperatures was completed, the temperature of the counter-current flow was raised, with rewarming to initial temperatures being accomplished in approximately 60–90 minutes. Data recording and VFT determinations were repeated at normothermic temperatures, and the animal subsequently euthanized.

The Ventricular Fibrillation Threshold (VFT) was measured via the pulse train technique, wherein a sequence of current pulses is applied through a set of ventricular electrodes during ventricular repolarization. For these studies a 100 Hz pulse train with 50% duty cycle was applied through the pair of ventricular electrodes. The pulse train was gated so that it began in the mid QT segment and extended just beyond the T wave in the scalar ECG, thereby scanning the vulnerable period and the immediately adjacent protective zone. The amplitude of the current pulse train was initially set at 2 mA and increased in 2 mA increments every 10 paced beats until ventricular fibrillation was initiated. The minimum current intensity resulting in ventricular fibrillation was taken as the VFT. The dimensionless quantity AEMI discussed above was calculated for both the QRS and ST-T wave segments for each of the data records, and compared to the corresponding VFT measurements. The results of these experiments will now be described.

Ten dogs were subjected to systemic hypothermia (lowering of core temperature to 29° C.). In seven (7) of these experiments, two sets of measurements were made (at pacing rates differing by at least 25 beats per minute), and in the remaining three (3) experiments, only one (1) measurement set could be made. In the seventeen (17) measurement sets, hypothermia reduced the measured VFT in all experiments, from a normothermic value of 23.8+/−2.5 mA (Mean+/−SEM) to a hypothermic value of 8.5+/−1.0 mA, corresponding to an average reduction of VFT by 61% (p<0.0001). The calculated AEMI(QRS) was found to increase in 16 of the 17 experiments, remaining unchanged (undetectable in the remaining measurement set (p<0.0001). The average AEMI(QRS) under normothermic conditions was found to be 3.7+/−3.0 ppm (Mean+/−SEM), while the same measure under hypothermic conditions increased to 1488+/−548 ppm. AEMI(ST-T) was found to increase in all 17 of the measurement sets, from a normothermic value of 43.9+/−18.4 ppm to a hypothermic value of 19178+/−5579 ppm (p<0.0001).

Ten dogs were subjected to transient Left Anterior Descending (LAD) coronary artery occlusion. Over the series of ten experiments, 24 different measurement sets were obtained. Coronary artery occlusion was accomplished by a decrease in the measured VFT in all 24 measurement sets, from a pre-occlusion value of 23.0+/−2.4 mA (Mean+/−SEM) to a value of 7.8+/−1.6 mA in the occluded state (p<0.0001), resulting in an average decrease in VFT by 61%. Occlusion was accompanied by an increase in AEMI(QRS) in 10 of the 24 measurement sets, no change (undetectable) in 11 of the 24 sets, and a decrease in AEMI(QRS) in 3 of the 20 sets (p<0.05). The average pre-occlusion value of AEMI(QRS) was 76.3+/−46.5 ppm (Mean+/−SEM), with the average in the occluded state being 245+/−111 ppm. AEMI(ST-T) was found to increase in 17 of the 24 measurement sets, remaining unchanged (undetectable) in 4 of the sets, and decreasing in 3 sets (p<0.002). The pre-occlusion average for AEMI(ST-T) was 842+/−505 ppm, and this increased to 1365+/−392 ppm with coronary artery occlusion.

Figure 2A:
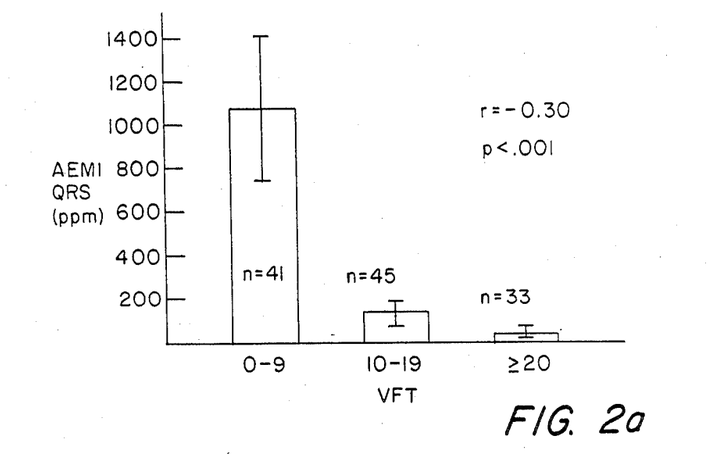
FIGS. 2a and 2b are histograms demonstrating that diminished electrical stability is accomplished by alternation in the ECG morphology.
Figure 2B:
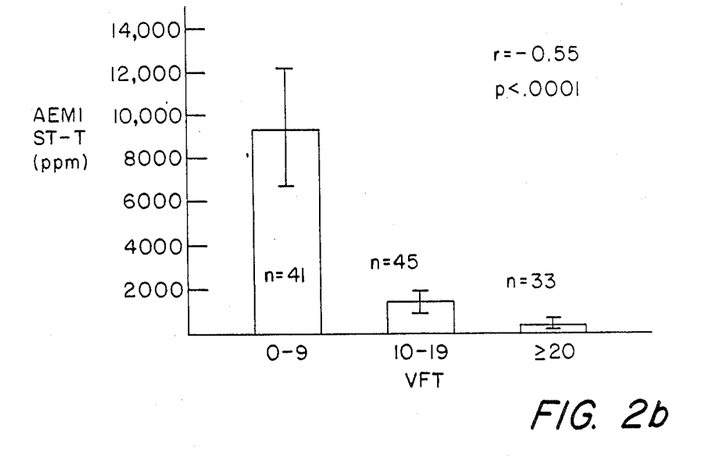

In total, 119 pairs of measurement sets (VFT and AEMI) were made in this series of animal experiments. FIGS. 2a and 2b are histograms showing the results of these experiments. The rank correlation coefficient between VFT and AEMI(QRS) was −0.30 (p<0.001), and that between VFT and AEMI(ST-T) was −0.55 (p<0.0001).

This set of animal experiments was to test: (1) the theoretical prediction of the existence of subtle alternation in ECG complex morphology under conditions of fixed rate pacing; and more importantly, (2) the prediction that such alternation serves as an indicator of decreased myocardial electrical stability. Cardiac electrical stability was measured via Ventricular Fibrillation Threshold determinations, and waveform alternation was quantified using the multidimensional spectral estimation approach of the present invention.

Hypothermia reproducibly diminished cardiac electrical stability, and this decrease in electrical stability was consistently accompanied by an increase in the measured alternation of ECG waveform morphology. Coronary artery occlusion also reproducibly diminished cardiac electrical stability, with somewhat less consistent, but still highly significant findings of increased ECG morphological alternation. It is perhaps important to remember that the hypothesized source of the alternating behavior is a subpopulation of myocardial cells which cannot respond reproducibly with every excitation wavefront, due to their recovery times exceeding the inter-beat interval. One might well expect that because coronary artery occlusion has relatively local effects compared to hypothermia, the size of the sub-population effected by coronary artery occlusion would be necessarily smaller, resulting in less of a detectable effect.

The results of the animal experiments confirm the existence of theoretically predicted subtle oscillations (alternation) in ECG morphology. A decrease in cardiac electrical stability was accompanied by an increase in the measured alternation in ECG complex morphology, and thus alternation of ECG morphology, in these experiments, served as a relative metric of electrical stability (i.e., an increase in alternation accompanied a decrease in stability). A stronger statement is made by the rank correlation of all VFT measurements with the associated AEMI metrics. The finding of highly significant (negative) correlations between VFT measurements and both QRS and ST-T wave alternation metrics suggest that alternation in ECG morphology may be useful as an absolute indicator of cardiac electrical stability.

It is thus seen that the objects of this invention have been achieved in that there has been disclosed method and apparatus for deriving an alternating ECG morphology index which correlates with myocardial electrical stability. Other modifications and variations of the above example will occur to those skilled in the art.

For instance, in the above example the ECG waveform morphology was computed on the vector magnitude of the ECG comprising the square root of the sum of the squares of the voltages measured in each of three orthogonal ECG leads. The advantage of using the vector magnitude is that it is relatively little affected by mechanical motion of the heart in the thorax. However, one may apply the method described above to individual ECG leads or if three orthogonal leads are available, one may compute the power spectra computed for each orthogonal lead and measure the extent of alternans in this summed spectrum. Theoretically, this will provide a more sensitive means of detecting alternans than the use of the vector magnitude, but will not as effectively identify alternans solely of electrical origin. This latter method will also detect alternans related to cardiac rotation and motion. However, this latter method may be preferable when mechanical alternans is not a confounding factor.

The example describe here analyzes beat-to-beat variability in ECG complex morphology specifically for the purpose of identifying electrical alternans using a spectral analysis method. The method of constructing a matrix of data from aligned ECG waveforms m(i, nT) can be used as a quite general, powerful non-degenerate method of analyzing beat-to-beat variability in ECG waveform morphology. In such an approach, analysis of variability in each column may be carried out and then an appropriate measure of that variability displayed for each column, summed over columns, or otherwise analyzed to provide a useful overall measure of the variability. For example, alternans could be measured in each column using a numerical technique different from the spectral method presented here. A time series domain method such as a linear or non-linear auto-regressive analysis technique could be used and might be less susceptible to error caused by disruption of the alternation sequence over several waveforms (e.g., by the appearance of ventricular premature beats).

Furthermore, it may well be that patterns of beat-to-beat variability other than alternans may be of diagnostic importance. Such patterns could be identified by analyzing variability in each column and computing one or more attributes of that variability for each column.

This attribute (or attributes) can be analyzed across columns by displaying the attribute (or attributes) as a function of column number in order to characterize the "attribute" waveform or characterize some feature of this "attribute" waveform by summing the attribute over column number or other such like techniques. Furthermore, the method of analysis presented here may be applied to other physiological waveforms such as blood pressure waveforms or respiratory waveforms, for analysis of waveform variability in order to ascertain physiologic regulation and stability.

It is recognized that these and other modifications and variations of the present invention will occur to those skilled in the art and it is intended that all such modifications and variations be included within the scope of the appended claims.

What is claimed is:

1. Method for analyzing cycle-to-cycle variability in a physiologic waveform for assessing relative physiologic stability, comprising:
   digitizing the waveform at a plurality of sample points for each cycle;
   constructing two-dimensional sample point matrices, having rows and columns, from the digitized waveform; and
   analyzing variability in each column of the sample point matrices to form an index correlating with the physiologic stability.

2. The method of claim 1 further including analyzing the variability by spectral analysis.

3. The method of claim 1 further including analyzing the variability by time series domain analysis.

4. Apparatus for analyzing cycle-to-cycle variability in a physiologic waveform for assessing relative physiologic stability, comprising:
   means for digitizing the waveform at a plurality of sample points for each cycle;
   means for constructing sample point matrices, having rows and columns, from the digitized waveform; and
   means for analyzing variability in each column of the sample point matrices to form an index correlating with the physiologic stability.

5. Method for deriving an alternating ECG morphology index from a series of heartbeats for assessing relative myocardial electrical stability, comprising:
   digitizing the ECG electrical signal waveform at a plurality of sample points for each of the beats;
   constructing sample point matrices, having rows and columns, from the digital ECG signal;
   computing the alternating energy at each of the sample points for the series of beats;
   summing the alternating energy over the entire set of sample points to generate a total alternating energy; and
   normalizing the total alternating energy with respect to energy of the average waveform, the normalized value being the alternating ECG morphology index, the index correlating with the myocardial electrical stability.

6. The method of claim 5 further including calculating a spectral noise estimate at a frequency band below the freqeuncy of the alternating energy and comparing the summation with the spectral noise estimate, the comparison being a test for significance.

7. The method of claim 5 further including estimating fiducial points for each of the beat signals.

8. The method of claim 5 further including low pass filtering the ECG electrical signals before digitizing the ECG signal waveform.

9. The method of claim 5 wherein the ECG signals are digitized by sampling at a rate of 1,000 samples per second.

10. Method for assessing relative myocardial electrical stability comprising determining the alternating ECG morphology index comprising:
    digitizing the ECG electrical signal waveform at a plurality of sample points for each of the beats;
    constructing sample point matrices, having rows and columns, from the digital ECG signal;
    computing the alternating energy at each of the sample points for the series of beats;
    summing the alternating energy over the entire set of sample points to generate a total alternating energy;
    normalizing the total alternating energy with respect to energy of the average waveform, the normalized value being the alternating ECG morphology index; and
    monitoring the changes in the alternating ECG morphology index;
    increases in this index correlating with lower myocardial electrical stability and vice versa.

11. Apparatus for deriving an alternating ECG morphology index from a series of heartbeats for assessing relative myocardial electrical stability, comprising:
    analog-to-digital means for digitizing the ECG electrical signal waveform at a plurality of sample points;
    means for constructing sample point matrices, having rows and columns, from the digitized ECG signals;
    digital computer means for computing the alternating energy at each of the sample points for the series of beats;
    computing means for summing the alternating energy over the entire set of sample points to generate a total alternating energy;
    computing means for calculating energy in an average ECG electrical signal waveform; and
    computing means for normalizing the total alternating energy with respect to energy of the average waveform, the normalized value being the alternating ECG morphology index, this index correlating with the myocardial electrical stability.

12. The apparatus of claim 11 further including 6-pole low-pass filtering amplifiers having a cutoff frequency of 360 Hz for receiving the ECG electrical signal waveform and passing a filtered signal to the analog-to-digital means.

13. The apparatus of claim 11 in which the computing means has a 2 Mbyte core memory.

14. The method of claim 1 wheren the physiologic waveform is a respiration waveform.

15. Method for analyzing cycle-to-cycle variability in an ECG for assessing relative myocardial electrical stability, comprising:
    digitizing the waveform at a plurality of sample points for each cycle;
    constructing two-dimensional sample point matrices, having rows and columns, from the digitzed waveform; and
    analyzing variability in each column of the sample point matrices to form an index correlating with the myocardial electrical stability.

16. Method for analyzing cycle-to-cycle variability in a blood pressure waveform for assessing relative stability of the blood pressure waveform, comprising:
- digitizing the waveform at a plurality of sample points for each cycle;
- constructing two-dimensional sample point matrices, having rows and columns, from the digitized waveform; and
- analyzing variabilty in each column of the sample point matrices to form an index correlating with the stability of the blood pressure waveform.

17. Method for analyzing cycle-to-cycle alternation in a physiologic waveform for assessing relative physiologic stability, comprising:
- digitizing the waveform at a plurality of sample points for each cycle;
- constructing two-dimensional sample point matrices, having rows and columns, from the digitized waveform; and
- analyzing alternation in each column of the sample point matrices to form an index correlating with the physiologic stability.

* * * * *

UNITED STATES PATENT AND TRADEMARK OFFICE
CERTIFICATE OF CORRECTION

PATENT NO. : 4,802,491

DATED : February 7, 1989

INVENTOR(S) : Richard J. Cohen et al.

It is certified that error appears in the above-identified patent and that said Letters Patent are hereby corrected as shown below:

Column 2, line 32, "accomplished" should be --accompanied--.

Column 7, line 31, "stuides" should be --studies--.

Signed and Sealed this

Twenty-fifth Day of July, 1989

Attest:

DONALD J. QUIGG

Attesting Officer

Commissioner of Patents and Trademarks